United States Patent [19]

Jacobs

[11] Patent Number: Plant 7,450

[45] Date of Patent: Feb. 19, 1991

[54] MINIATURE ROSE PLANT NAMED FOUTWIST (LEMON TWIST)

[76] Inventor: Betty A. Jacobs, 525 Butler Rd., Bakersfield, Calif. 93304

[21] Appl. No.: 413,380

[22] Filed: Sep. 27, 1989

[51] Int. Cl.[5] ..... A01H 5/00

[52] U.S. Cl. ..... Plt./8

[58] Field of Search ..... Plt./8, 7

[56] References Cited

U.S. PATENT DOCUMENTS

P.P. 5,358 11/1984 Williams ..... Plt. 8

*Primary Examiner*—Howard J. Locker

[57] ABSTRACT

The subject of the present disclosure is a new and distinct variety of miniature rose plant characterized by bright yellow buds and flowers of good substance and keeping qualities.

1 Drawing Sheet

1

The present invention relates to a new and distinct variety of hardy, dwarf, bush type rose plant of the miniature class: the variety being primarily characterized — as to novelty — by bright yellow (near Lemon Yellow 4/1) buds and flowers, the general color effect being bright yellow.

The variety is further characterized by:

An abundance of bloom, with flowers, on mature plant, borne both singly and several together in loose spray or cluster.

Light tea fragrance.

A plant which is vigorous, of rounded, somewhat upright shape with semi-glossy, small foliage with pointed leaflets; the buds and flowers being similar in form to Starina (Miniature — U.S. Plant Pat. No. 2,646— expired).

The plant, which has a normal height of 14 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Four Seasons Rose Nursery, located at Bakersfield, California, under conditions of careful control and observation, as a cross between Gold Badge (Floribunda — U.S. Plant Pat. No. 4,625) as the seed parent and Great Day (Miniature — U.S. Plant Pat. No. 5,358) as the pollen parent.

Subsequent to origination of the variety I successfully reproduced it at my nursery, located as aforesaid, by budding as well as by cuttings; the reproductions have run true in all respects.

The color photograph illustrates the variety, including the foliage, buds, and flowers.

Referring now specifically to the new and distinct variety of rose plant, the following is a detailed description thereof in outline; all major color plate identifications being by reference to the British Colour Council Horticultural Colour Chart, except where common terms of color definition are employed.

Type: Hardy; dwarf; bushy; rounded; upright; seedling; greenhouse; outdoors; cut flowers; garden decoration.

Class: Miniature.

*International identification.*—Variety: Foutwist.

2

*Commercial synonym.*—Lemon Twist.

Flowers borne: Often singly but also in loose sprays of 3 to 5 or more on slender wirey stems.

Quantity of bloom: Abundant both outside and in greenhouse.

Bud:

*Peduncle.*—Average length; slender but sturdy; erect; medium green.

*Hairs.*—Few or none.

*Before calyx breaks; size.*—Small. Form long; pointed with several small foliaceous apendages and several very small hairs on surface of bud; with foliaceous parts extending beyond the tip of the bud equal to one-half or more to its length.

*Color.*—Medium green (near Lettuce Green 861/1 or lighter). As calyx breaks, color — yellow (near Aureolin Yellow 3/1)

*Opening.*—Opens well in all weather.

Bloom:

*Size when fully open.*—Small, averaging about 35–40 mm ($1\frac{1}{4}$ to $1\frac{1}{2}$).

*Petalage.*—Double — averaging from about 30 to 45 petals arranged regularly (more double than Great Day, its paternal parent), plus often several small petaloids.

*Form.*—High centered (more so than Great Day, its paternal parent), then becoming more rounded with petals reflexing outward, and, later at maturity, folding or quilling to points (resembling a star as it opens, whereas Great Day does not). Open flowers may show stamens.

Petals: Fairly thick (heavier substance than Great Day, the paternal parent, and not as thick as Gold Badge, the maternal parent), velvety on inside and satiny on outside surface.

*Shape.*—Outside petals, broad lanceolate with acute tip; intermediate — broad lanceolate with acute tip; inside — lanceolate with acute tip.

Color: Newly opened flower from a plant grown in plastic greenhouse (March, 1989), Bakersfield, Calif.

*Outside petal.*—Outside surface — ranging from near Aureolin Yellow 3/1 to near Lemon Yellow 4/1 on entire surface. Inside surface — near Lemon Yellow 4/1.

*Intermediate petal.*—Outside surface similar to outside petal. Inside surface — similar to outside petal.

*Inner petal.*—Outside surface — similar to intermediate petal. Inside surface — similar to intermediate petal. General color effect; newly opened flowers — bright yellow (near Lemon Yellow 4/1). Three days open — ages slightly lighter on outer half or ⅔ of petal near tip — color near Lemon Yellow 4/2. Behavior — opens well in all weather. Spent petals usually do not drop off. Flower longevity (March 1989) — plant in pot — 4–5 days or longer. Cut flowers at living room temperature 4–5 days.

Reproductive organs:

*Stamens.*—Numerous (approximately 60) arranged regularly about pistils.

*Filaments.*—Varying length, short to medium, yellow.

*Anthers.*—Golden Yellowish (deeper color than those of Great Day, its paternal parent)

*Pollen.*—Not Abundant (less than that of Great Day, its paternal parent).

*Pistils.*—(Not as abundant as those on Great Day, its paternal parent, and slightly shorter).

*Styles.*—Fairly even; short length; bunched; color — light yellow.

*Ovaries.*—All enclosed in calyx.

*Hips.*—Few in number, ball shaped, light orange.

*Sepals.*—Permanent; long and spear shaped; recurved against peduncle.

*Seed.*—Few.

Foliage:

*Leaves.*—Compound of five (sometimes three or seven) leaflets; small to medium; leathery; semi-glossy.

*Leaflets.*—Shape: broad, lanceolate; apex acute; base rounded (sometimes acute). Margin serrate.

*Color.*—Medium green (near Spinach Green o960/1 or lighter); new growth — normal (medium) green (near Spinach Green o960/1 or lighter).

*Rachis.*—Medium strength; upperside usually quite smooth, grooved; underside sparsely thorny (very small) with few or no tiny prickles.

*Stipules.*—Short to medium length; narrow to medium width; short length; narrow points which turn out usually at about 45 degrees.

Disease resistance: Better than average resistance to rose diseases mildew and blackspot.

Growth:

*Habit.*—Dwarf; very bushy; rounded to upright; much branched.

*Growth.*—Free, vigorous; internodes short.

*Canes.*—Medium slender; sturdy.

*Main Stems.*—Color: medium green.

*Thorns.*—Moderate amount. Prickles — moderate.

*Branches.*—Color: medium green. Thorns: moderate. Prickles: few to none. Hairs: none.

The miniature rose plant and its flowers as herein described may vary in slight detail due to climatic, soil, and cultural conditions under which the variety may be grown; the present description being of the variety as grown at Bakersfield, Calif.

The following is claimed:

1. A new and distinct variety of miniature rose plant of hardy, dwarf, very bushy, rounded to upright, much branched habit; substantially as illustrated and described, characterized by buds and flowers of bright yellow (near Lemon Yellow 4/1 or similar); the bud and flower resembling the variety Starina (U.S. Plant Pat. No. 2,646) in form; and further characterized by a plant of vigorous and compact growth habit, said plant being more bushy and compact than Great Day (its paternal parent), with flowers being slightly smaller, of greater average petalage, and more abundant than on Great Day; easy to propagate from cuttings or by budding, with an abundance of small to medium size semi-glossy foliage (color near Spinach Green o960/1 or lighter) and an abundance of flowers borne both singly and in loose clusters of 3 to 5 or more.

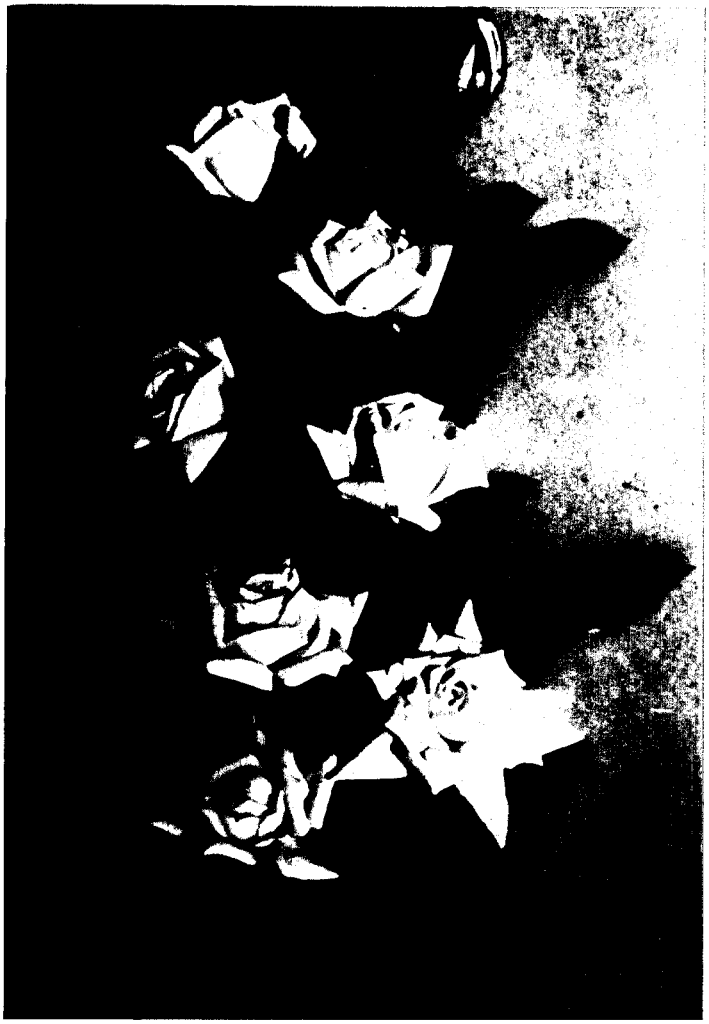

* * * * *